(12) United States Patent
Job et al.

(10) Patent No.: US 8,309,732 B2
(45) Date of Patent: Nov. 13, 2012

(54) PROCESS FOR PREPARING QUATERNARY SALTS OF PIPERIDYL ESTERS OF MANDELIC ACID

(75) Inventors: Andreas Job, Köln (DE); Denys Baskakov, Leverkusen (DE); Ralf Krahwinkel, Langenfeld (DE); Antje Hieronymi, Köln (DE)

(73) Assignee: Saltigo GmbH, Langenfeld, DE (US)

( * ) Notice: Subject to any disclaimer, the term of this patent is extended or adjusted under 35 U.S.C. 154(b) by 183 days.

(21) Appl. No.: 12/418,847

(22) Filed: Apr. 6, 2009

(65) Prior Publication Data
US 2009/0270629 A1    Oct. 29, 2009

(30) Foreign Application Priority Data

Apr. 25, 2008   (DE) .......................... 10 2008 020 746

(51) Int. Cl.
*C07D 211/46* (2006.01)
(52) U.S. Cl. ..................................................... 546/222
(58) Field of Classification Search .................... 546/222
See application file for complete search history.

(56) References Cited

U.S. PATENT DOCUMENTS

| 2,956,062 A | 10/1960 | Lunsford et al. ........... 260/326.3 |
| 4,022,787 A | 5/1977 | Soldati et al. ............ 260/293.81 |
| 2007/0292375 A1 | 12/2007 | Woehrmann et al. ........... 424/68 |

FOREIGN PATENT DOCUMENTS

| EP | 1302458 | 4/2003 |
| GB | 788126 | 12/1957 |
| WO | WO2006/066929 | 6/2006 |

OTHER PUBLICATIONS

Journal of the American Chemical Society, 1956, 78, p. 3701.
European Search from co-pending Application EP 09 15 7753 dated Jul. 17, 2009.

*Primary Examiner* — Kristin Bianchi
(74) *Attorney, Agent, or Firm* — Michael A. Miller

(57) ABSTRACT

What is described is a process for preparing compounds of the general formula (I)

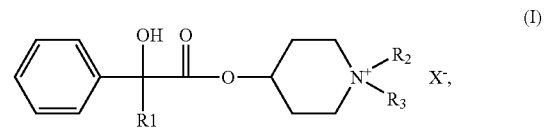

in which $R_1$, $R_2$ and $R_3$ independently of one another represent hydrogen, an alkyl group or an aryl group, wherein compounds of the general formula (II)

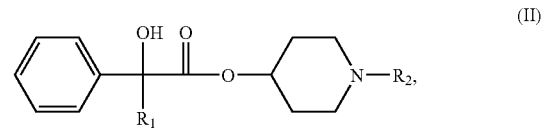

in which $R_1$ and $R_2$ have the meaning given for formula (I), are reacted with an alkylating agent of the general formula (III)

$$R_3X \quad (III),$$

in which X represents a halogen atom and $R_3$ has the meaning given for formula (I), if appropriate in a solvent.

5 Claims, No Drawings

PROCESS FOR PREPARING QUATERNARY SALTS OF PIPERIDYL ESTERS OF MANDELIC ACID

The present invention relates to a process for preparing substituted quaternary salts of piperidyl esters of mandelic acid by reaction with an alkylating agent.

Quaternary salts of piperidyl esters of mandelic acid are used, inter alia, in pharmaceutically active compounds, cosmetics and agrochemicals.

The synthesis of quaternary salts of piperidyl esters of mandelic acid by reacting piperidyl esters of mandelic acid with an alkylating agent is described in GP 788126. However, this process has the disadvantage that the solvent used is carcinogenic benzene and that the purity of the crude products obtained is low, requiring an additional recrystallization of crude products. From U.S. Pat. No. 2,956,062 and the Journal of the American Chemical Society 1956, 78, 3701, it is furthermore known that quaternary salts of piperidyl esters of mandelic acid can be obtained by reacting piperidyl esters of mandelic acid in the solvent diethyl ether with an alkylating agent. However, on an industrial scale, owing to a high tendency to form peroxides, the handling of large amounts of diethyl ether is associated with a high safety risk and should thus be avoided. Furthermore, this process, too, has the disadvantage of a low purity of the crude products obtained, requiring an additional recrystallization of crude products.

Owing to the high importance of substituted quaternary salts of piperidyl esters, there was therefore a need for providing a process for their preparation which avoids the disadvantages described above.

Accordingly, it was an object of the present invention to provide a process which in a relatively simple manner and in high yields, allows the preparation of quaternary salts of piperidyl esters, which process can also be carried out on an industrial scale.

The present invention provides a process for preparing compounds of the general formula (I)

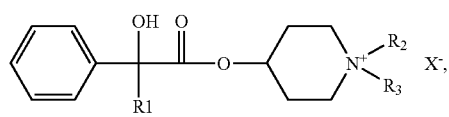

(I)

in which $R_1$, $R_2$ and $R_3$ independently of one another represent hydrogen, an alkyl group or an aryl group, characterized in that compounds of the general formula (II)

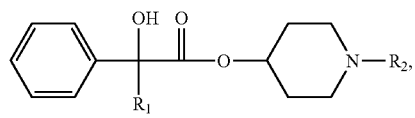

(II)

in which $R_1$ and $R_2$ have the meaning given above,
are reacted with an alkylating agent of the general formula (III)

$$R_3X \quad \quad \quad (III),$$

in which X represents a halogen atom.

Preferably, $R_1$ represents a $C_3$-$C_{20}$-cycloalkyl radical and $R_2$ represents a $C_1$-$C_{20}$-alkyl radical. Very particularly preferably, $R_1$ represents a cyclopentyl or cyclohexyl radical and $R_2$ represents a methyl or ethyl radical.

Alkylating agents of the formula (II) are alkyl halides, the bromides and iodides being preferred, the bromides being particularly preferred. Preferred alkyl radicals $R_3$ are $C_{1-20}$-alkyl and $C_3$-$C_{20}$-cycloalkyl. Particular preference is given to straight-chain $C_1$-$C_{20}$-alkyl radicals. Particularly preferably, $R_3$ is a methyl radical, i.e. in this case $R_3$—X is methyl bromide.

Reaction temperature of the process according to the invention can, for example, be in a range of from $-100$ to $300°$ C., preferably in a range of from $-20$ to $100°$ C. Particularly preferably, the reaction is carried out at room temperature (20 to $25°$ C.).

The reaction pressure for the process according to the invention can, for example, be in the range of from 1 hPa to 20 MPa, preferably from 100 hPa to 2 MPa. Particularly preferably, the reaction is carried out at atmospheric pressure.

The process according to the invention can be carried out in a solvent. Suitable solvents are, for example, aprotic solvents, such as, for example, the esters of carboxylic acids, such as, for example, ethyl acetate, butyl acetate, benzyl benzoate, or aromatic and aliphatic halogenated hydrocarbons, such as, for example, chlorobenzene, dichlorobenzene, dichloromethane, chloroform or carbon tetrachloride. It is also possible to use nitriles, such as, for example, acetonitrile, propionitrile or benzonitrile, or amides, such as, for example, N,N-dimethylformamide, N,N-dimethylacetamide, N-methylformanilide, N-methylpyrrolidone or hexamethylphosphoric amide, and also sulphur compounds, such as, for example, sulpholane, and aliphatic halogenated hydrocarbons, or mixtures thereof. Particular preference is given to aliphatic halogenated hydrocarbons. Very particularly preferably, the solvent used is dichloromethane.

It is also possible to carry out the reaction without any added solvent. This applies in particular when the starting material of the formula (II) is liquid under the reaction conditions.

Preferred starting material concentrations in the reaction solution are from 1% by weight to 100% by weight, particularly preferably from 10 to 50% by weight, very particularly preferably from 10 to 25% by weight.

The reaction is carried out, for example, by initially charging the compounds of the formula (II), if appropriate with the addition of solvent, and adding the alkylating agent of the formula (III) or, if appropriate, its solution in a solvent. Alternatively, it is also possible to initially charge the alkylating agent, if appropriate in a solvent, followed by the addition of the starting material or its solution in a solvent. Also possible is the simultaneous metering in of starting materials of the formula (II) and the alkylating agent of the formula (III).

The procedure according to the invention gives, in a single step, in high chemical yield and after simple work-up, the desired quaternary salts of piperidyl esters of mandelic acid.

The compounds of the formula (I) which can be prepared according to the invention are suitable in particular for preparing agrochemicals, pharmaceutically active compounds, fragrances and aromas, flavours, active compounds for the cosmetic industry and for polymers.

EXAMPLES

Example 1

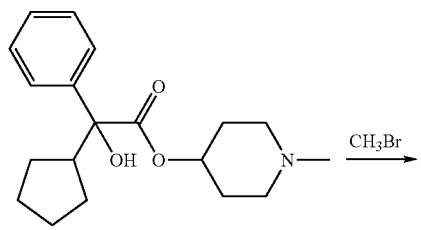

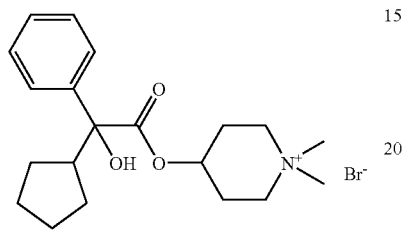

Dichloromethane (2500 ml) was initially charged in a 6 litre double-jacketed reactor, and bromomethane (150 g, 1.579 mol) was initially charged at 5-10° C. At 10-15° C., a solution of 1-methyl-4-piperidyl α-cyclopentylmandelate in heptane (100 g, 0.237 mol, 75%) was then metered in. Remaining bromomethane (401 g, 4.22 mol) was metered into a reaction mixture simultaneously with the solution of 1-methyl-4-piperidyl α-cyclopentylmandelate (737 g, 1.744 mol, 75%). The reaction solution was brought to room temperature and stirred under nitrogen overnight. Dichloromethane (1033 g) was added to the reaction solution, and the solvent was then distilled off under atmospheric pressure. The product suspension was filtered through a pressure nutsche filter and washed with dichloromethane (1550 g), acetone (2195 g) and ethyl acetate (2195 g) and dried. The yield was 804 g (98% of theory).

Example 2

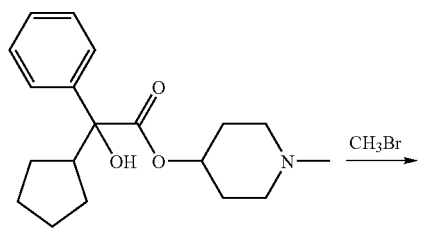

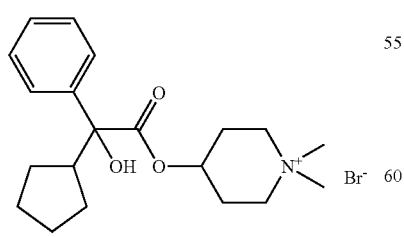

A solution of 1-methyl-4-piperidyl α-cyclopentylmandelate (663 g, 1.61 mol, 77%) in heptane was initially charged in a 6 litre double-jacketed reactor, and dichloromethane (2500 ml) was added. At 20° C., bromomethane (458 g, 4.82 mol) was then introduced. The reaction solution was stirred at room temperature under nitrogen overnight. Some of the solvent was distilled off under atmospheric pressure (943 g). The product suspension was filtered through a pressure nutsche and washed with dichloromethane (1944 g), acetone (1590 g) and ethyl acetate (2211 g) and dried. The yield was 654 g (98% of theory).

The invention claimed is:

1. Process for preparing compounds of the general formula (I)

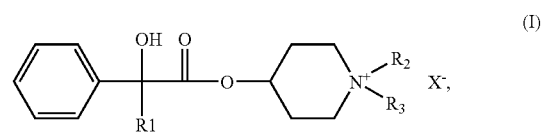

in which $R_1$ is a $C_3$-$C_{20}$-cycloalyl radical, $R_2$ is a $C_1$-$C_{20}$-alkyl radical, and $R_3$ is a $C_1$-$C_{20}$-alkyl radical or $C_3$-$C_{20}$-cycloalkyl radical, wherein compounds of the general formula (II)

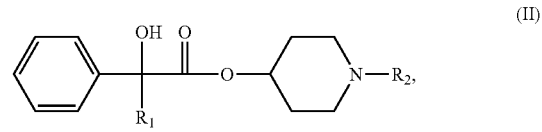

in which $R_1$ and $R_2$ have the meaning given for formula (I), are reacted with an alkylating agent of the general formula (III)

in which X represents a halogen atom and $R_3$ has the meaning given for formula (I), and wherein the alkylating agent is initially charged in dichloromethane as the solvent and the compound of formula (II) is, if appropriate, is metered into the reaction.

2. Process according to claim 1, wherein $R_1$ represents a cyclopentyl radical and $R_2$ represents a methyl radical.

3. Process according to claim 1, wherein X represents a bromine or iodine atom and $R_3$ represents a $C_1$-$C_{20}$-alkyl radical or a $C_3$-$C_{20}$-cycloalkyl radical.

4. Process according to claim 1, wherein X represents a bromine atom and $R_3$ represents a methyl radical.

5. Process according to claim 1, wherein the compound of the general formula (II) is 1-methyl-4-piperidyl α-cyclopentylmandelate.

* * * * *